United States Patent [19]

Whitted et al.

[11] Patent Number: 4,510,247

[45] Date of Patent: Apr. 9, 1985

[54] USE OF GLUCOSE OXIME TO INCREASE GLUCOSE ISOMERASE ACTIVITY IN BACTERIAL CELLS

[75] Inventors: Beth E. Whitted; George Boguslawski, both of Elkhart, Ind.

[73] Assignee: Miles Laboratories, Inc., Elkhart, Ind.

[21] Appl. No.: 465,243

[22] Filed: Feb. 9, 1983

[51] Int. Cl.$^3$ .................. C12N 9/92; C12N 9/38; C12R 1/19; C12R 1/20
[52] U.S. Cl. .................. 435/207; 435/200; 435/234; 435/849; 435/850
[58] Field of Search ............... 435/207, 234, 850, 200, 435/201, 202, 205, 206

[56] References Cited

U.S. PATENT DOCUMENTS 4,283,496 8/1981 Lee ...................................... 435/253

*Primary Examiner*—Lionel M. Shapiro
*Attorney, Agent, or Firm*—Jerome L. Jeffers

[57] ABSTRACT

Disclosed is a method of increasing the production of enzymes involved in carbohydrate metabolism by bacterium of the species *F. arborescens* or *E. coli*. The method involves growing the bacterium on an aqueous nutrient medium containing glucose oxime.

3 Claims, No Drawings

USE OF GLUCOSE OXIME TO INCREASE GLUCOSE ISOMERASE ACTIVITY IN BACTERIAL CELLS

BACKGROUND OF THE INVENTION

The preparation of D-glucose oxime is reported by Finch, et al in *J. Chem. Soc.*, Perkins Trans. I, 1682–1685, 1975. This sugar derivative is useful in studies on conformation of sugars in aqueous solutions. Glucose oxime is a potent inhibitor of glucose isomerase activity in vitro.

It has now been discovered that the presence of glucose oxime in the nutrient medium will, under appropriate conditions, increase the production of enzymes involved in carbohydrate metabolism in certain species of bacteria, in vivo.

SUMMARY OF THE INVENTION

The present invention is a method of increasing the production of enzymes involved in carbohydrate metabolism by a bacterium capable of producing such enzymes which bacterium is selected from the species *Flavobacterium arborescens* or *Escherichia coli*. The method comprises growing the bacterium in an aqueous nutrient medium containing glucose oxime, but employing a carbon source other than glucose, in a concentration sufficient to cause an increase in the production of the enzyme.

DESCRIPTION OF THE INVENTION

In practicing the present invention, the bacterium can be grown in a minimal nutrient medium containing salts, vitamins, and a carbon source to which has been added glucose oxime. Increased enzyme production is observed with most carbon sources; however, when glucose is employed, enzyme production decreases. This is the case because glucose causes strong "catabolite repression" (Warner, et al, *J. Bacter.*, 136, 947–955, 1978).

It has been observed that the presence of glucose oxime causes the increase of glucose isomerase production by a bacterium from the species *F. arborescens* and an increase in β-galactosidase production during fermentation of *F. arborescens* and also of a bacterium from the species *E. coli*. The production of other enzymes involved in carbohydrate metabolism can be stimulated in organisms of these species capable of producing such enzymes because glucose oxime appears to counteract the catabolite repression effect of carbohydrates.

While the presence of glucose oxime will stimulate the production of enzyme at certain concentrations, it has been discovered that the enzyme production reaches a peak and then declines as the concentration of glucose oxime increases. The optimal concentration of glucose oxime varies from species to species and from strain to strain within a particular species. However, one skilled in the art can readily determine the level of glucose oxime necessary for maximum enzyme production without undue experimentation.

In addition to increasing enzyme production in particular bacterial species, the glucose oxime technique can be used to screen particular strains for their ability to produce enhanced quantities of enzymes useful in carbohydrate metabolism. This can be achieved by selecting mutants resistant to glucose oxime by virtue of the fact that they are permanently derepressed (insensitive to catabolite repression). In the case of glucose isomerase, the mutants with elevated levels of the enzyme could acquire resistance by simply titrating out the inhibitor.

The method of practicing the present invention is further illustrated by the following examples:

EXAMPLE I

Inhibition of the Growth of *F. arborescens* by Glucose Oxime

Cells of *F. arborescens* were grown in a minimal medium containing the following on a weight/volume (w/v) basis: 0.05% $K_2HPO_4$; 0.03% KOH; 0.02% $MgSO_4$; 0.001% $FeSO_4$; 0.05% $(NH_4)_2SO_4$; 0.5% casamino acids; 0.001% cysteine; 2 ml/l vitamins and 2 ml/l trace elements. The vitamin solution contained the following (mg/l): 0.005 biotin; 0.100 calcium pantothenate; 0.005 folic acid; 0.100 niacinamide; 0.050 p-aminobenzoic acid; 0.100 pyridoxine; 0.050 riboflavin and 0.100 thiamine. The trace element solution contained the following (mg/l): 0.5 $ZnCl_2$; 0.03 $CuSO_4.5H_2O$; 0.05 $MnCl_2$; 0.01 $Cr_2(SO_4)_3$; 0.02 $H_2MoO_4$; 0.05 $H_3BO_3$ and 0.05 $NiCl_2.6H_2O$.

The pH of the minimal medium was adjusted to 7.0. The carbon source was at a concentration of 0.2% (w/v).

The cells were grown at 30° C. in a New Brunswick Scientific shaker at 250 rpm in 50 ml of minimal medium containing 0.2% xylose and increasing concentrations of glucose oxime. The initial cell density was 5 Klett units (green filter). After 28 hours, the extent of growth was measured. Two strains were used, the wild-type strain (xylose-inducible), ATCC 4358, and a mutant strain, NRRL B 11,022, which produces glucose isomerase constitutively. The cell growth, measured at varying concentrations of glucose oxime, is set out in Table I.

TABLE I

| Concentration of Glucose Oxime (%) | Growth (Klett Units) | |
|---|---|---|
| | Wild-Type ATCC 4358 | NRRL B 11,022 |
| 0 | 435 | 455 |
| 0.05 | 307 | 450 |
| 0.1 | 120 | 330 |
| 0.2 | 10 | 106 |
| 0.4 | 13 | 39 |

These data demonstrate that the growth is increasingly inhibited by increasing concentrations of glucose oxime. The wild-type strain is inhibited by 75% at approximately 0.1% glucose oxime and the mutant at approximately 0.2% glucose oxime. This difference in sensitivities may reflect a difference in glucose isomerase levels between the two strains (see example II).

EXAMPLE II

Effect of Glucose Oxime on Glucose Isomerase Activity In Vivo

Cells were grown as described in example I. After 24 hours, the cells were harvested, washed with glucose isomerase assay buffer in the manner described by Boguslawski, et al in *J. Appl. Biochem.*, 2:367–372, 1980, and resuspended to equal cell densities. Glucose isomerase activity was assayed according to the method disclosed in the *J. Appl. Biochem.* cited above. The activity of each strain, expressed in μmol of fructose produced in 30 minutes per $10^{10}$ cells, is set out in Table II.

TABLE II

| Concentration of Glucose Oxime (%) | Glucose Isomerase Activity | |
|---|---|---|
| | Wild-Type ATCC 4358 | NRRL B 11,022 |
| 0 | 15.3 | 50.1 |
| 0.05 | 26.7 | 61.2 |
| 0.1 | 33.3 | 81.0 |
| 0.2 | 27.3 | 91.2 |
| 0.4 | 15.6 | 63.6 |

From Table II it can be determined that glucose isomerase activity increased with increasing concentrations of glucose oxime up to a maximum and then decreased.

EXAMPLE III

Effect of Various Carbon Sources on Stimulation of Glucose Isomerase Activity by Glucose Oxime The constitutive strain NRRL B 11,022 was used in this example in which glucose isomerase activity was measured with and without the presence of glucose oxime in nutrient media containing differing carbon sources. The results of this experiment are set out in Table III.

TABLE III

| Carbon Source (0.2%) | Glucose Isomerase Activity | |
|---|---|---|
| | No Addition | Glucose Oxime (0.2%) |
| Xylose | 50.1 | 91.2 |
| Arabinose | 46.1 | 97.2 |
| Lactose | 67.8 | 88.8 |
| Glucose | 17.7 | 16.5 |

With those carbon sources other than glucose it was observed that glucose isomerase activity increased in the presence of glucose oxime. However, glucose repressed the enzyme activity and glucose oxime could not overcome this inhibition.

EXAMPLE IV

Effect of Glucose Oxime on β-Galactosidase Activity In Vivo

Cells were grown in minimal medium containing 0.2% xylose or 0.2% lactose with or without 0.1% glucose oxime. Yeast extract (0.1%) was included when *E. coli* cells were used. The cells were harvested, washed, and resuspended to equal cell density with assay buffer and β-galactosidase activity was assayed according to the method disclosed by Platt, et al in J. H. Miller, *Experiments in Molecular Genetics,* Cole Spring Harbor Laboratory Press, Cold Harbor, N.Y., 1972. The activity is expressed as increase in absorbance at 420 nanometers ($\Delta A_{420\,nm}$) due to the release of o-nitrophenol. The results of this experiment are set out in Table IV.

TABLE IV

| | β-Galactosidase Activity ($\Delta A_{420}$/hr) | | |
|---|---|---|---|
| | *F. arborescens* | | |
| Carbon Source | Wild-Type ATCC 4358 | NRRL B 11,022 | *E. coli\** NK 6701 |
| Xylose | 0.089 | 0.080 | 0.40 |
| Lactose | 0.468 | 0.505 | 18.40 |
| Lactose & Glucose Oxime | 0.871 | 1.177 | 26.00 |

*Obtained from Coli Genetic Stock Center, Yale University School of Medicine, New Haven, CT.

Lactose is needed for induction of the enzyme and glucose oxime increases the activity further.

EXAMPLE V

Immunotitration of Glucose Isomerase in Extracts From Cells of *F. arborescens* ATCC 4355 Grown in the Absence or Presence of Glucose Oxime Extracts prepared from *F. arborescens* ATCC 4355 cells grown in minimal medium containing xylose alone (control) or xylose and 0.1% glucose oxime were treated with increasing amounts of rabbit immune serum prepared against purified glucose isomerase. The reaction mixtures contained 392 μg of control extract protein or 196 μg of extract protein from cells grown in the presence of glucose oxime.

After incubation and removal of precipitated antibody-antigen complexes, the residual glucose isomerase activity was measured in the manner previously described. The maximal activity (100%) was 15.75 μmole of fructose formed in 30 minutes for both extracts. Thus, the specific activity of glucose isomerase from cells grown in the presence of glucose oxime was exactly twice that of the control. Accordingly, the amount of antiserum necessary for the complete removal of glucose isomerase activity from the reaction mixture was almost twice as high for the glucose oxime sample as for the control extract (ratio of antiserum protein to the extract protein: 5.8-vs-3.2). This indicates that glucose oxime acts to increase the amount of enzyme protein in cells rather than to stimulate the enzyme activity.

What is claimed is:

1. A method of increasing the production of enzymes involved in carbohydrate metabolism by a bacterium capable of producing such enzyme which bacterium is selected from the species of *Flavobacterium arborescens* or *Escherichia coli* which method comprises growing the bacterium in an aqueous nutrient medium containing glucose oxime, but employing a carbon source other than glucose, wherein the concentration of glucose oxime is sufficient to cause an increase in the production of the enzyme.

2. The method of claim 1 wherein the carbon source is xylose, arabinose or lactose.

3. The method of claim 1 wherein the bacterium is *F. arborescens* ATCC 4358 or NRRL B 11,022.

* * * * *